(12) United States Patent
Bell

(10) Patent No.: US 11,723,599 B2
(45) Date of Patent: Aug. 15, 2023

(54) LOWER EXTREMITY DIAGNOSTIC DEVICE

(71) Applicant: Tawaun Bell, Warner Robins, CA (US)

(72) Inventor: Tawaun Bell, Warner Robins, CA (US)

(73) Assignee: Tawaun Bell, Los Gatos, CA (US)

( * ) Notice: Subject to any disclaimer, the term of this patent is extended or adjusted under 35 U.S.C. 154(b) by 347 days.

(21) Appl. No.: 16/902,853

(22) Filed: Jun. 16, 2020

(65) Prior Publication Data

US 2021/0045684 A1 Feb. 18, 2021

Related U.S. Application Data

(60) Provisional application No. 62/886,253, filed on Aug. 13, 2019.

(51) Int. Cl.
*A61B 5/026* (2006.01)
*A61B 5/00* (2006.01)

(52) U.S. Cl.
CPC .......... *A61B 5/6807* (2013.01); *A61B 5/0035* (2013.01); *A61B 5/0077* (2013.01); *A61B 5/0261* (2013.01); *A61B 5/6843* (2013.01); *A61B 5/7425* (2013.01)

(58) Field of Classification Search
CPC ... A61B 5/6807; A61B 5/6829; A61B 5/0059; A61B 5/0062; A61B 5/0064; A61B 5/0066; A61B 5/0068; A61B 5/0071; A61B 5/0073; A61B 5/0075; A61B 5/0077; A61B 5/0082; A61B 5/0261; A61B 5/1455–14558; A43B 3/44; A43B 3/34; A43B 3/36
See application file for complete search history.

(56) References Cited

U.S. PATENT DOCUMENTS

| | | | | |
|---|---|---|---|---|
| 5,991,648 | A * | 11/1999 | Levin | A61B 5/14552 600/344 |
| 6,519,484 | B1 * | 2/2003 | Lovejoy | A61B 5/6838 600/323 |
| 2002/0026109 | A1 * | 2/2002 | Diab | A61B 5/14552 600/323 |
| 2010/0016733 | A1 * | 1/2010 | Smith | A61B 5/0295 600/483 |
| 2014/0052006 | A1 * | 2/2014 | Lee | A61B 5/7455 600/479 |
| 2014/0316292 | A1 * | 10/2014 | McRae | G16H 40/63 600/504 |
| 2015/0073271 | A1 * | 3/2015 | Lee | A61B 5/02007 600/475 |
| 2017/0027454 | A1 * | 2/2017 | Korposh | A61B 5/6892 |
| 2019/0125195 | A1 * | 5/2019 | Hielscher | A61B 5/0073 |
| 2019/0159728 | A1 * | 5/2019 | Pritchard | A61B 8/4209 |
| 2020/0145797 | A1 * | 5/2020 | Craig | A61B 5/4585 |
| 2020/0205736 | A1 * | 7/2020 | Gamboa-Pinto | A61B 5/6829 |
| 2021/0393200 | A1 * | 12/2021 | Bunn | A61B 5/01 |
| 2022/0142495 | A1 * | 5/2022 | De Marco | A61B 5/0261 |

* cited by examiner

*Primary Examiner* — Colin T. Sakamoto
(74) *Attorney, Agent, or Firm* — Fish & Richardson P.C.

(57) ABSTRACT

In one aspect, a device includes a shoe sole; a set of toe wraps engaged with the shoe sole; and at least one infrared device rotatably connected to a particular toe wrap among the set of toe wraps.

20 Claims, 7 Drawing Sheets

LOWER EXTREMITY DIAGNOSTIC DEVICE

CROSS-REFERENCE TO RELATED APPLICATIONS

This application claims the benefit under 35 U.S.C. § 119(e) of U.S. Patent Application No. 62/886,253, entitled "LOWER EXTREMITY DIAGNOSTIC DEVICE," filed Aug. 13, 2019. The disclosure of the foregoing application is incorporated herein by reference in its entirety for all purposes.

BACKGROUND

This specification relates to a diagnostic device that aids in the evaluation of lower extremities.

Analysis of data obtained about lower extremities can be helpful in diagnosing a number of health issues. However, to obtain the information needed to aid in the diagnosis, many different pieces of equipment may be needed, which can increase the delay in obtaining the diagnosis and make it more difficult to obtain the information needed.

SUMMARY

In general, one innovative aspect of the subject matter described in this specification can be embodied in a device that includes a shoe sole; a set of toe wraps engaged with the shoe sole; and at least one infrared device rotatably connected to a particular toe wrap among the set of toe wraps. These and other embodiments can each optionally include one or more of the following features.

The shoe sole can include a bottom layer; an intermediate layer; and a top layer. The intermediate layer can include one or more computing components that facilitate collection of information from sensors included in, or attached to, the device. The sensors can include a three-dimensional camera and the infrared device. The top layer can include one or more pressure sensors.

The infrared device can be rotatable across at least one hundred eighty degrees.

The set of toe wraps can include at least one toe wrap that includes a camera that is arranged to capture images of objects that are positioned between the at least one toe wrap and a heel end of the shoe sole.

The device can include one or more processors that combine information obtained from each of the infrared device and the camera. The one or more processors can output the combined information from the infrared device and the camera to a display device. The combined information visually presents various physical changes to a foot or leg that was captured by the camera. The physical changes can include at least blood flow as detected using the infrared device.

In general, one innovative aspect of the subject matter described in this specification can be embodied in a system that includes one or more data processing apparatus; and a diagnostic device including: a shoe sole; and a set of toe wraps engaged with the shoe sole; and at least one infrared device rotatably connected to a particular toe wrap among the set. These and other embodiments can each optionally include one or more of the following features.

The shoe sole can include a bottom layer; an intermediate layer; and a top layer. The intermediate layer can include one or more computing components that facilitate collection of information from sensors included in, or attached to, the device. The sensors can include a three-dimensional camera and the infrared device. The top layer can include one or more pressure sensors. The set of toe wraps can include at least one toe wrap that comprises a camera that is arranged to capture images of objects that are positioned between the at least one toe wrap and a heel end of the shoe sole.

The one or more processors can be configured to combine information obtained from each of the infrared device and the camera. The one or more processors can output the combined information from the infrared device and camera to a display device. The combined information visually presents various physical changes to a foot or leg that was captured by the camera.

In general, one innovative aspect of the subject matter described in this specification can be embodied in a method that includes the operations of capturing, by an infrared device rotatably connected to a particular toe wrap among a set of toe wraps of a shoe, infrared data of a foot or leg of a person wearing the shoe; capturing, by a camera arranged to capture images of objects that are positioned between the particular toe wrap and a heel end of the shoe, images of the foot or the leg of the person wearing the shoe; combining the infrared data and the images to create combined information about the foot or the leg of the person wearing the shoe; and outputting the combined information to present various physical changes to the foot or the leg that were captured by the infrared device. The physical changes can include at least blood flow as detected using the infrared device.

Particular embodiments of the subject matter described in this specification can be implemented so as to realize one or more of the following advantages. The diagnostic device discussed throughout this document can provide for faster collection of information needed to make a medical diagnosis, facilitate synchronization of the information collected, and present the collected information as combined data that can provide a more complete representation of the physical state of a lower extremity (e.g., foot, ankle, or leg).

The details of one or more embodiments of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
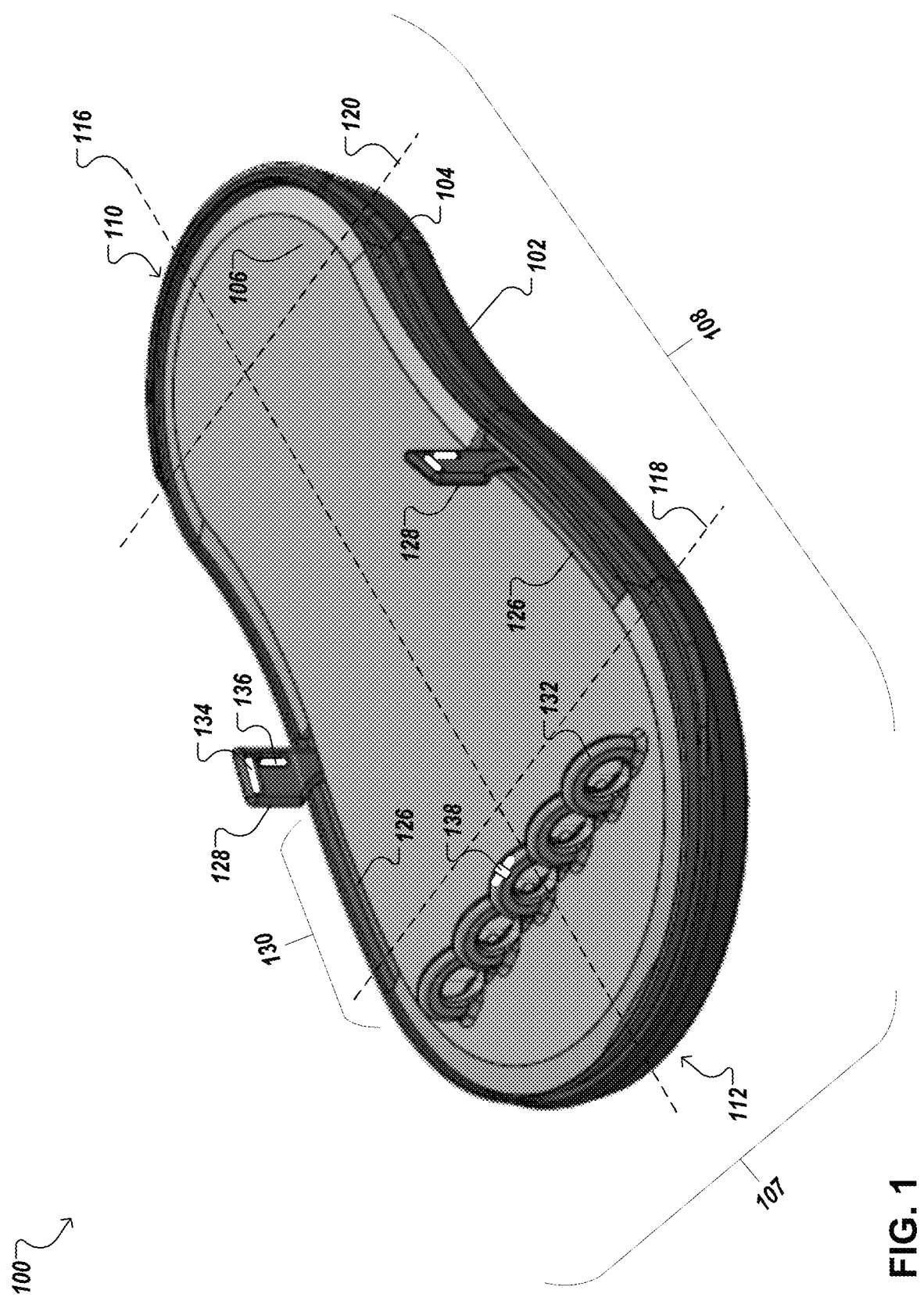
FIG. 1 is an illustration of an example diagnostic device.

FIG. 1 is an illustration of an example diagnostic device 100. The diagnostic device 100 has a sole that includes a bottom layer 102, an intermediate layer 104, and a top layer 106. The bottom layer 102 can be made of rubber or another appropriate material, and have a shape that generally corresponds to a shape of a foot. More specifically, the bottom layer 102 can have a width 107 that varies along a length 108 of the bottom layer 102, where the length 108 extends from a heel end 110 of the diagnostic device 100 to a toe end 112 of the bottom layer 102.

For example, the bottom layer 102 can have a smallest width at a midpoint axis 114 that is defined between the heel end 110 and the toe end 112 and perpendicular to (or at least intersects) a length axis 116 defined by the length 108 of the bottom layer 102. The bottom layer 102 can have larger widths at a toe portion axis 118 and a heel portion axis 120 that are respectively offset from the toe end 112 and the heel end 110. For example, the toe portion axis 118 can be located between the toe end 112 and the midpoint axis 114, while the heel portion axis 120 can be located between the heel end 110 and the midpoint axis 114. In some implementations, the toe portion axis 118 and the heel portion axis 120 can cross both sides of the bottom layer 102 and, in some situations, parallel to each other. The widths of the bottom layer 102 can vary depending on the application and/or dimensions of the foot to which the diagnostic device 100 is being fitted. As discussed in more detail with reference to FIG. 2, the bottom layer 102 can have a sole ridge 122 that extends away from a plane defined by a bottom of the bottom layer 102.

The intermediate layer 104 can have a shape that corresponds to the shape of the bottom layer 102. The dimensions of the intermediate layer 104 can be substantially the same as the dimensions of the bottom layer 102 or incrementally smaller than the dimensions of the bottom layer 102 so that the intermediate layer 104 can be inserted into the bottom layer 102. For example, the dimensions of the intermediate layer 104 can be specified so that an intermediate layer ridge 124 is in contact with the sole ridge 122 when the intermediate layer 104 is placed on top of (or into) the bottom layer 102. The intermediate layer 104 can be glued or otherwise affixed to the bottom layer 102 during the manufacturing process. As discussed in more detail with reference to FIG. 2, the intermediate layer 104 can include a pair of clasp slots 126 that are formed to accept a clasp(s) 128. The intermediate layer 104 can be made of rubber or another appropriate material.

As discussed in more detail below, the intermediate layer 104 can include various components that facilitate collection of information about a person's toes, feet, and/or legs when the diagnostic device 100 is worn. For example, the intermediate layer 104 can include one or more flexible PCBs that include data processors, memory devices, and other computing components. The information can be collected from one or more infrared cameras, one or more three-dimensional scanning cameras ("3D cameras"), and/or other components that facilitate the collection of information about a foot, leg, and/or toes (e.g., temperature reading components). The intermediate layer 104 can also include communications components, such as near field communication circuits, BLUETOOTH® circuits, and/or Wi-Fi circuits. While the computing and communications components are described as being located in the intermediate layer 104, other portions of the diagnostic device 100 can house the computing and/or communications components. For example, the computing and/or communications components could be located in the bottom layer 102 or the top layer 106.

The top layer 106 can have a shape that corresponds to the shape of the bottom layer 102 and/or the intermediate layer 104. The dimensions of the top layer 106 can be the same as those of the bottom layer 102 and/or intermediate layer 104, or incrementally smaller than the dimensions of the bottom layer 102 and/or intermediate layer 104 so that the top layer 106 can be inserted into the intermediate layer 104 or overlay the intermediate layer 104. For example, the dimensions of the top layer 106 can be specified so that the top layer 106 is in contact with the intermediate layer ridge 124 and/or sole ridge 122 when the top layer 106 is placed on top of (or into) the intermediate layer 104. The top layer 106 can be glued or otherwise affixed to the intermediate layer 104 and/or bottom layer 102 during the manufacturing process to form a solid base of the diagnostic device 100.

The top layer 106 can be made of a translucent material. As discussed in more detail below, the top layer 106 can be made of, or include, one or more pressure pads that collect pressure information when the diagnostic device 100 is worn on a foot. The pressure information that is collected can provide insight as to the distribution of weight on the foot and portions of the foot that are bearing the most weight. The pressure information can be transmitted, or otherwise transferred, to the data processors and or memory devices of the diagnostic device 100.

As discussed in more detail below, the top layer 106 can be formed with a pair of clasp notches 130 that align with the pair of clasp slots 126 of the intermediate layer 104. The clasp notches 130 allow for the clasps 128 to extend vertically away from the diagnostic device 100 when the top layer 106 is affixed to the intermediate layer 104 and/or bottom layer 102, as shown.

The top layer 106 includes a set of toe wraps 132 that can include a single toe wrap or multiple toe wraps. The set of toe wraps 132 are located between the midpoint axis 114 and the toe end 112 of the top layer 106. The set of toe wraps 132 can be formed of the same material as the top layer 106, or the set of toe wraps 132 can be made of a different material than the top layer 106. In some implementations, the set of toe wraps 132 is formed using a material that is elastic in nature, so that the set of toe wraps 132 will stretch to fit toes that are inserted into the set of toe wraps 132. For example, the set of toe wraps 132 can be made of a silicon material, such as Dragon Skin™, that is capable of stretching to receive a wide variety of toe sizes, while also providing a snug fit.

The set of toe wraps 132 can be formed to be oval or circular in shape. Openings in the set of toe wraps 132 can be sized as appropriate to receive toes of a foot. As can be appreciated, different variations of the diagnostic device 100 can have sets of toe wraps 132 of varying sizes to accommodate placement on feet and/or toes of different sizes.

The set of toe wraps 132 can include a variety of components that facilitate the collection of additional information about the toes, foot, and/or leg when the diagnostic device 100 is worn. For example, the set of toe wraps 132 can include one or more flexible PCBs that include components that collect information about the toes, foot, and/or leg, process that collected information, and/or communicate with other devices. For example, the flexible PCBs can include near field communication circuits, BLUETOOTH® circuits, Wi-Fi circuits, memory components, processors, and/or other components that facilitate the collection, processing, and communication of information about a foot or toes that are inserted into the diagnostic device 100, as well as the leg.

In some implementations, the diagnostic device 100 includes the clasps 128. The clasps 128 are configured to accept a strap that secures the diagnostic device 100 to a foot. For example, as discussed in more detail below, each of the clasps 128 can have a main strap void 134 defined therein, and a strap can be fed through each of the main strap voids 134 and secured to prevent the diagnostic device 100 from falling off of the foot. In some implementations, the strap can be secured using hook and loop so that the strap can be readily adjusted and secured to fit various size feet. In some implementations, snaps or other mechanisms can be used to secure the strap once it has been adjusted to fit the foot.

In some implementations, the clasps 128 can be configured to include a heel strap void 136. The heel strap void 136 can be similar to the main strap void 134, but be aligned so that a strap inserted into the main strap void 134 on both sides of the diagnostic device 100 extends toward the heel end 110 of the bottom layer 102. The strap that is fed through the main strap void 134 on both sides of the diagnostic device 100 can be adjusted to limit movement of the diagnostic device 100 as a person wearing the diagnostic device 100 walks.

The set of toe wraps 132 can have an infrared device 138 attached thereto. The infrared device 138 can be rotatably attached to the set of toe wraps 132 so that the infrared device 138 can be adjusted to capture different infrared information for different parts of a foot or leg of the person wearing the diagnostic device 100. In some implementations, the infrared device 138 can be configured to rotate at least 180 degrees, or some other specified amount.

Figure 2:
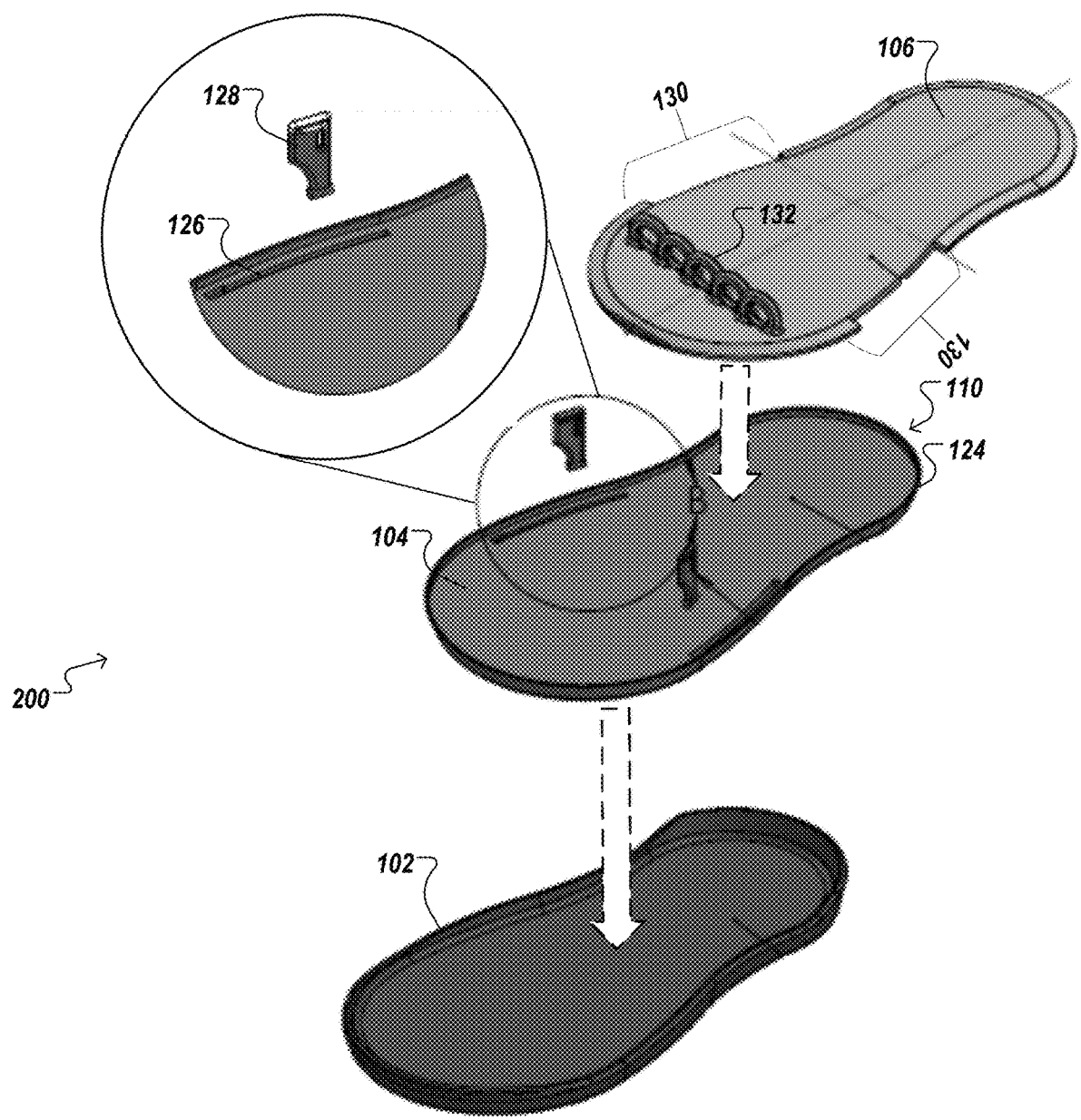
FIG. 2 is an exploded view of the diagnostic device.

FIG. 2 is an exploded view 200 of the diagnostic device 100. The exploded view 200 more clearly shows how the intermediate layer 104 can be inserted into the bottom layer 102, and the top layer 106 can be inserted into (or placed over) the intermediate layer 104 during the manufacturing process. The exploded view 200 also shows how the clasps 128 can be inserted into the pair of clasp slots 126. The clasps 128 can be formed so that the clasps 128 "lock" into the pair of clasp slots 126 when the clasps 128 are inserted into the pair of clasp slots 126 a specified depth. Although the clasps 128 are "locked" into the pair of clasp slots 126, they are formed so that the clasps 128 can slide back and forth along the length of the pair of clasp slots 126. The ability to slide the clasps 128 back and forth along the length of the pair of clasp slots 126 enable the strap received by the clasps 128 to be relocated as desired to fit the foot that is wearing the diagnostic device 100. For example, when the diagnostic device 100 is placed on a smaller foot, the clasps 128 can be moved toward the set of toe wraps 132, while the clasps 128 can be moved away from the set of toe wraps 132 (e.g., toward the heel end 110) when the diagnostic device 100 is being placed on a larger foot.

The exploded view 200 also shows example locations of the clasp notches 130 in the top layer 106. As shown, the clasp notches 130 can be created by discontinuations on the edges of the top layer 106 at locations that correspond to the locations of the pair of clasp slots 126 when the top layer 106 is placed on top of (or inserted into) the intermediate layer 104. In some implementations, the clasp notches 130 could be voids that are within the edge of the top layer 106 (e.g., rather than discontinuations of the edge) at locations that correspond to the locations of the pair of clasp slots 126 when the top layer 106 is placed on top of the intermediate layer 104.

Figure 3:
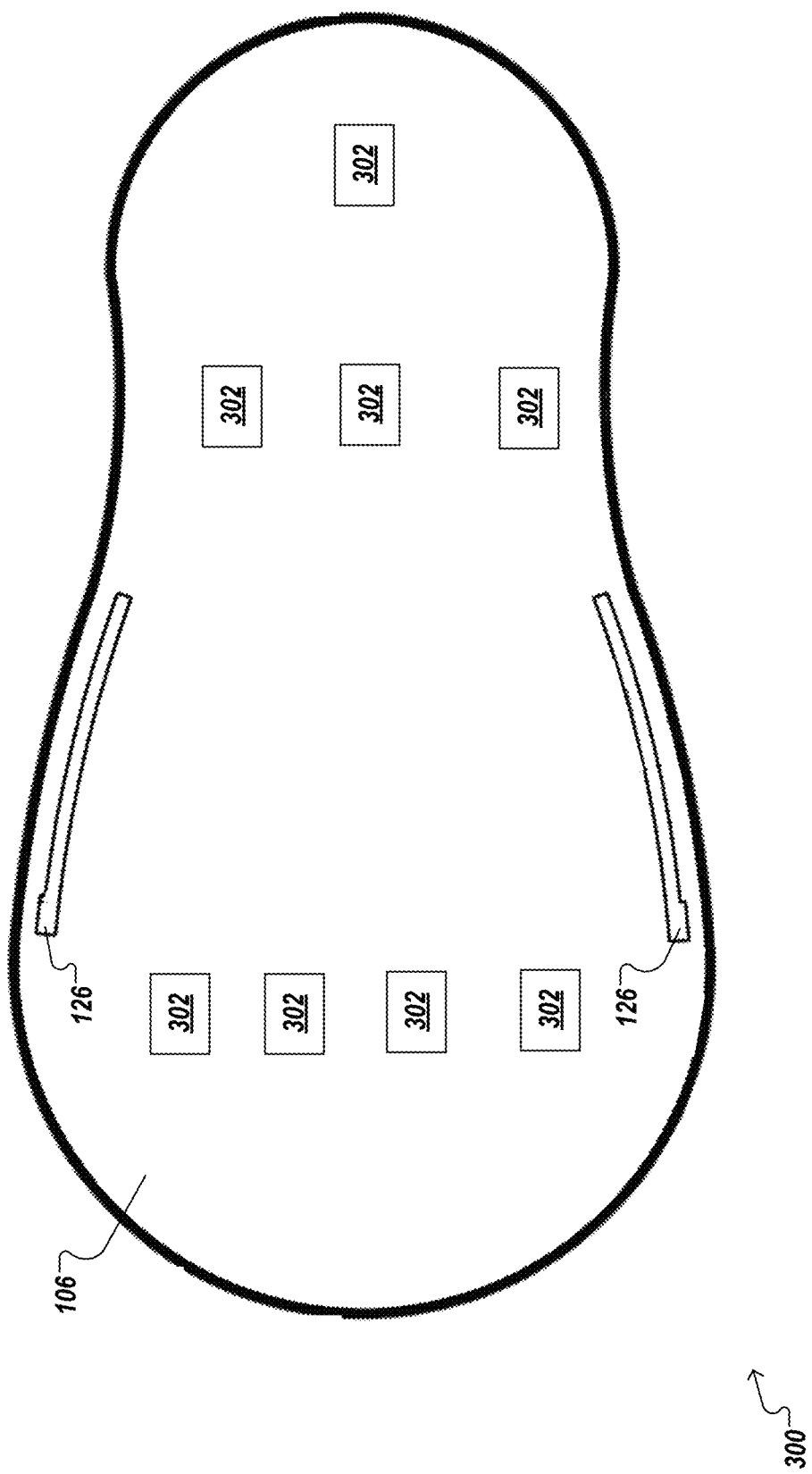
FIG. 3 is an example top view of the top layer.

FIG. 3 is an example top view 300 of the top layer 106. The top view 300 of the top layer 106 shows further details of the clasp notches 130, and their relative locations along the periphery of the top layer 106. The top view 300 also shows example locations of pressure sensors 302 in the top layer 106. Note that fewer or additional sensor locations can be used, and that the positioning of the pressure sensors 302 can be varied. The pressure sensors 302 can collect pressure information corresponding to how weight is distributed across the foot when a person is standing and/or walking. This pressure information can be communicated to processors in the intermediate layer 104 or the set of toe wraps 132 (e.g., by way of conductors or wireless communications) and/or to other devices that are otherwise in communication with the pressure sensors 302 (e.g., a nearby mobile device, tablet device, diagnostic equipment, or data processing apparatus). For example, the top layer 106 can include a NFC circuit or BLUETOOTH® circuit that is capable of transmitting the pressure information to a connected device, such as a nearby computer station or diagnostic equipment.

Figure 4:
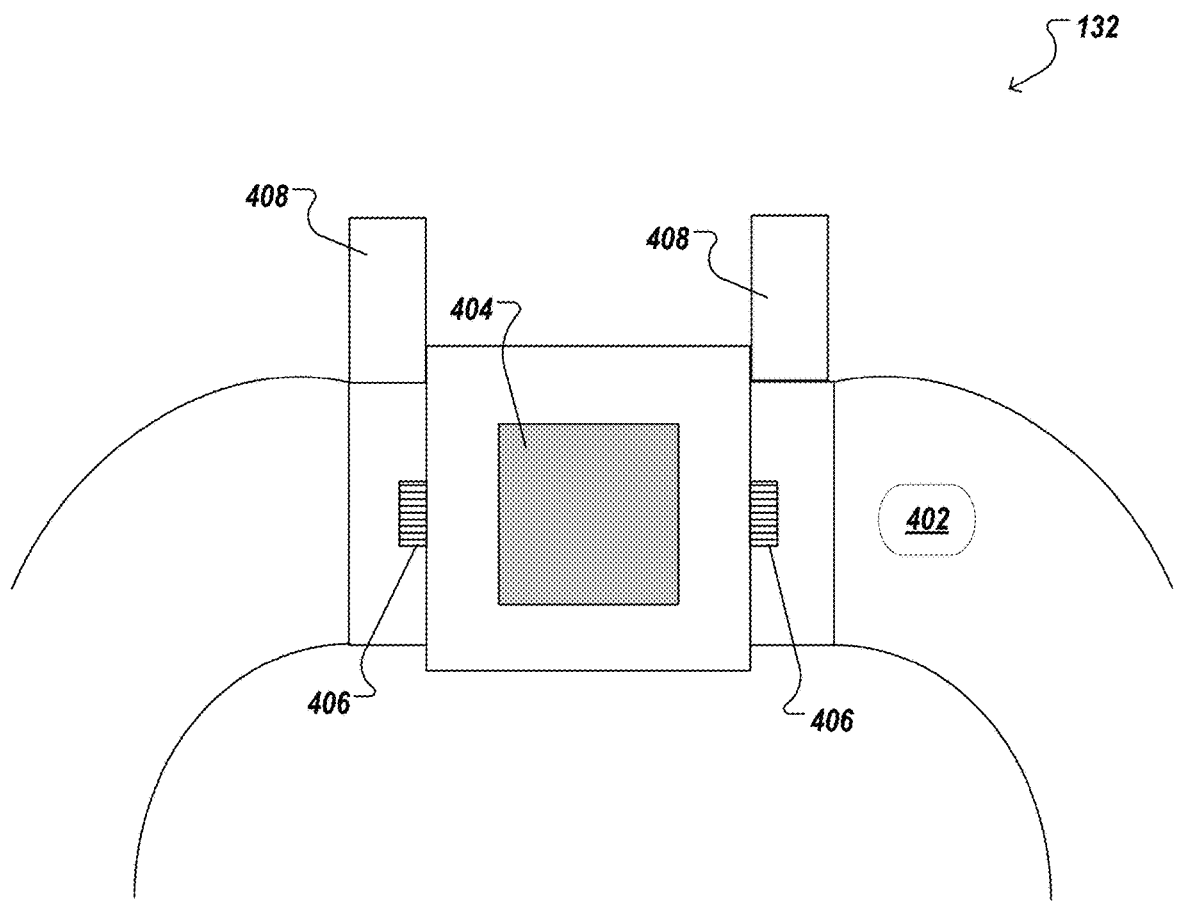
FIG. 4 is an illustration of an example set of toe wraps.

FIG. 4 is an illustration of an example set of toe wraps 132. The set of toe wraps 132 includes a camera 402 and an infrared sensor 404. As shown, the infrared sensor 404 is rotatably attached to (or integrated into) the set of toe wraps 132, thereby enabling the infrared sensor 404 to obtain infrared information at various different angles and directions, and can be rotated up to 360 degrees, or over any desirable range. For example, the infrared sensor 404 can be positioned so that it is pointed at, and collecting information from, toes of a foot, a top side of the foot, an ankle, or a lower part of a leg. As such, the infrared sensor 404 can collect infrared information from these various parts of the leg/foot, which is used to determine blood flow characteristics and other information related to the health of the toes, foot, and/or leg.

In some implementations, the rotation of the infrared sensor 404 is facilitated by rotation wheels 406 that are connected to, or formed as part of, the case of the infrared sensor 404. Alternatively, the infrared sensor 404 can be secured to a single rotation wheel that extends from one side of the infrared sensor 404 to the other side of the infrared sensor 404. The rotation wheels 406 can include ridges that allow for rotation of the infrared sensor 404 to be incrementally changed (e.g., by clicking into place). In some implementations, one or more position lock mechanisms 408 can secure the infrared sensor 404 in position. For example, the position lock mechanisms 408 can rotate open and closed so as to allow for free rotation of the rotation wheels 406 when the position lock mechanisms 408 are open (as shown), and secure the rotation wheels 406 in position when the position lock mechanisms 408 are closed. In some implementations, the position lock mechanisms 408 are fixed (i.e., do not open and close), but rather allow for limited rotation of the rotation wheels 406. For example, the position lock mechanisms 408 can include stop mechanisms (not shown) that generally maintain the position of the rotation wheels 406 (and infrared sensor 404), but allow the rotation wheels 406 (and infrared sensor 404) to be rotated when sufficient rotational force is applied thereby causing the ridges to pass by a locking mechanism (e.g., a ridge or tab) in the position lock mechanisms 408. In this example, the rotation of the rotation wheels 406 to a new position can create an audible click that informs the user that the rotation wheels 406 (and infrared sensor 404) has been adjusted to a new position.

In some implementations, the camera 402 is a three-dimensional camera that captures images that convey the perception of depth to generate three dimensional images. The camera 402 can be located at virtually any part of the set of toe wraps 132, and/or embedded into the set of toe wraps 132. Generally, the camera 402 will be located on a side of the camera 402 that is facing the heel end 110 so that the camera 402 can capture images of a foot and/or leg when a toe is inserted into the set of toe wraps 132. In FIG. 4, the camera 402 is shown as located offset from the infrared sensor 404, but in some implementations, the camera 402 can be co-located with the infrared sensor 404, such that the camera 402 can be rotatably adjusted along with the infrared sensor 404, as discussed above.

In operation, the camera 402 captures images (or videos) of toes, a foot, and/or leg, while the infrared sensor 404 simultaneously captures infrared data about the toes, foot, and/or leg. These images and infrared data can be transmitted to a data processing apparatus (e.g., the data processors in the top layer 106 or an external data processing apparatus), where the data can be aggregated, processed, and/or analyzed. For example, the infrared data can be overplayed and aligned, both visibly and temporally, with the captured images from the camera 402 to create a combined view of the collected information. The combined view of the information can visually present blood flow information, temperature information, and other information within the images. For example, the combined view can visually depict the relative blood flow of the toes, foot, and/or leg within the images, and other diagnostic information.

Figure 5:
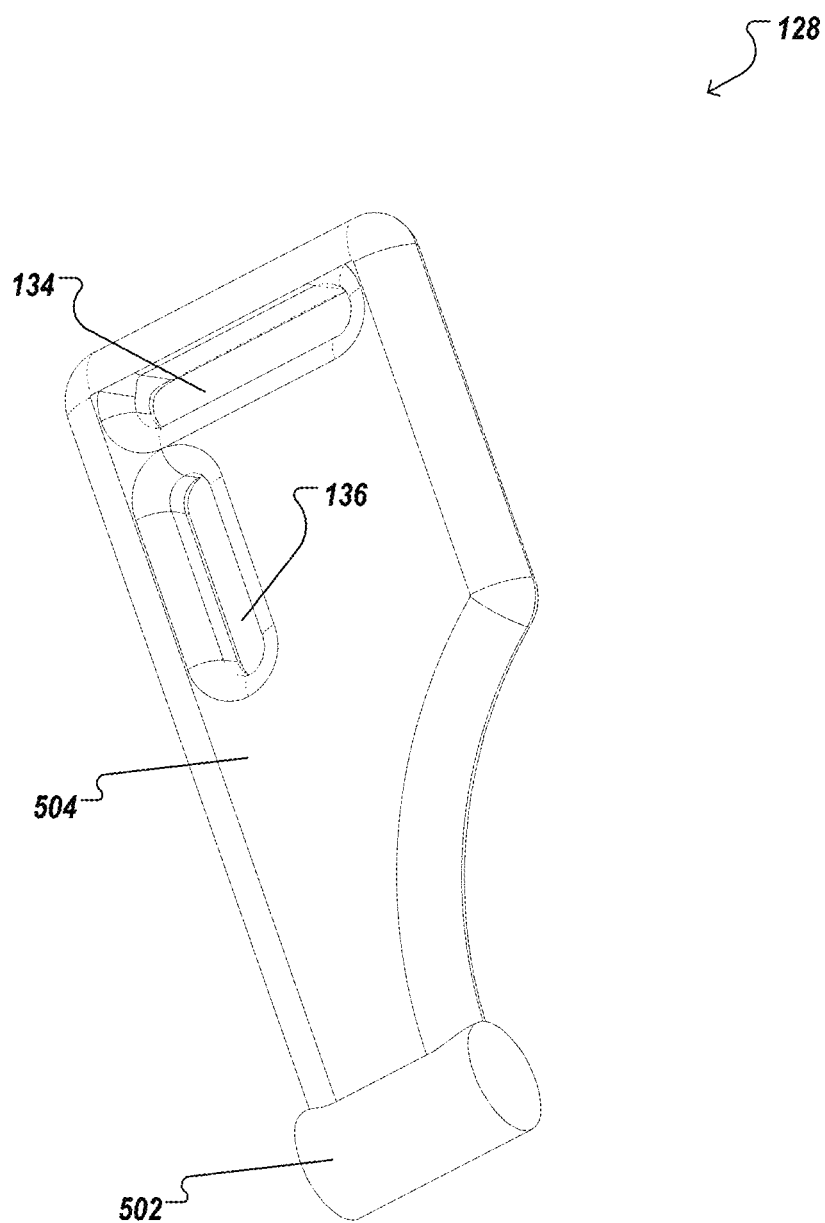
FIG. 5 is an example illustration of the clasps.

FIG. 5 is an example illustration of the clasps 128. The illustration of the clasps 128 shows the main strap void 134 and the heel strap void 136 in more detail. As seen in FIG. 5, the main strap void 134 and the heel strap void 136 can be formed in an "L" configuration, such that the main strap void 134 and the heel strap void 136 are substantially perpendicular to each other, although that configuration is not required. As such, straps that are inserted through the main strap void 134 and the heel strap void 136 will be guided in different directions to facilitate the securing of the diagnostic device 100 to a top portion of a foot and a heel portion of the foot.

The illustration of FIG. 5 also shows a securing mechanism 502 of the clasps 128. The securing mechanism 502 secures the clasps 128 to the diagnostic device 100 when the securing mechanism 502 is inserted into the pair of clasp slots 126 of the intermediate layer 104. For example, the enlarged thickness of the securing mechanism 502 relative to a main body 504 of the clasps 128 allows for the intermediate layer 104 to recompress after the securing mechanism 502 has passed though the pair of clasp slots 126 of the intermediate layer 104, thereby securing the clasps 128 into place. The securing mechanism 502 is shown as being cylindrical in shape, but other shapes can be used (e.g., a wedge shape, an oval shape, or any other appropriate shape).

Figure 6:
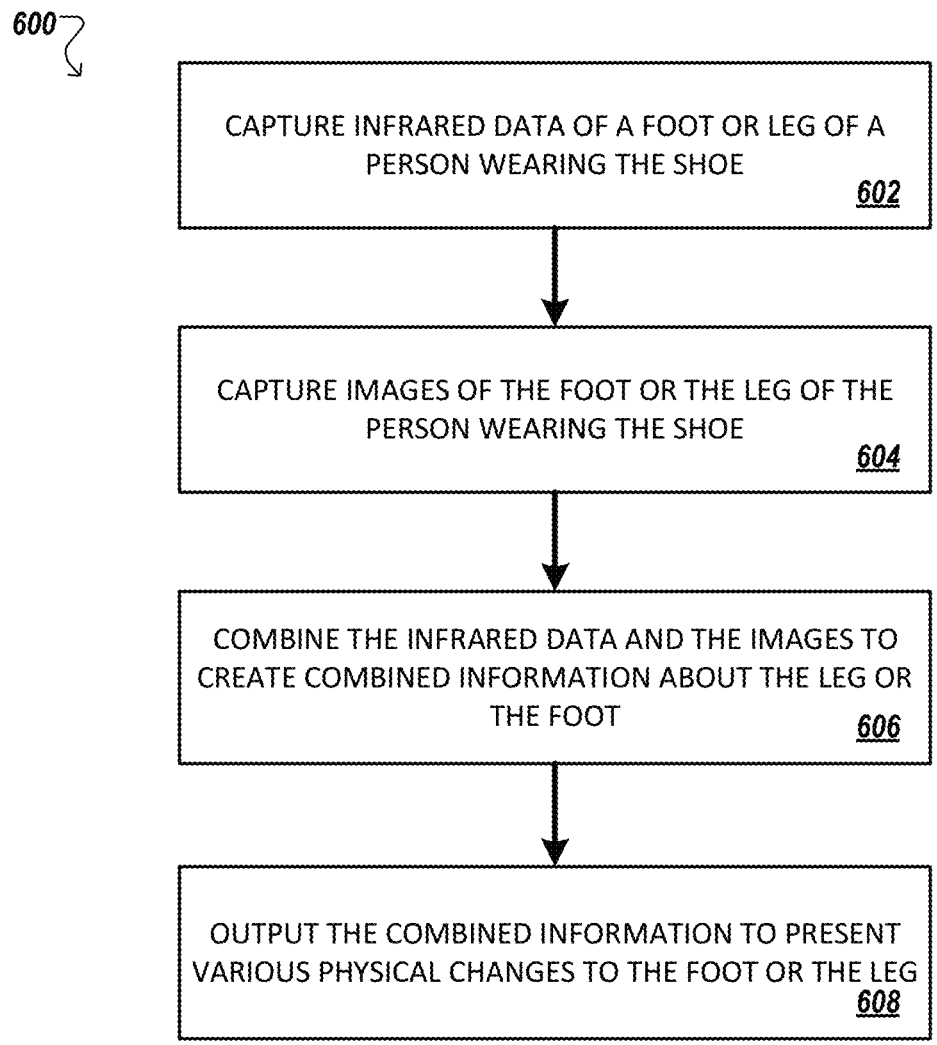
FIG. 6 is a flow chart of an example process that can be implemented using the diagnostic device.

FIG. 6 is a flow chart of an example process 600 that can be implemented using the diagnostic device 100. Operations of the process 600 can be implemented using one or more data processing apparatus or an appropriate system that includes the one or more data processing apparatus. In some implementations, at least some of the operations of the process 600 can be carried out using sensors and/or computing devices of the diagnostic device 100 described above. Operations of the process 600 can be implemented as instructions stored a non-transitory computer readable medium that when executed by one or more data processing apparatus, cause the one or more data processing apparatus to perform the operations of the process 600.

Infrared data of a foot or leg of a person wearing a shoe is captured (602). In some implementations, the infrared data can be captured using an infrared device, as discussed above. The infrared device can be connected to a particular toe wrap among a set of toe wraps of a shoe. In some situations, the infrared device is rotatably connected to the particular toe wrap, and enables the infrared device to rotate to obtain infrared data at different angles and for different parts of a foot or leg. The rotation of the infrared device can be throughout three hundred sixty degrees or limited as desired (e.g., limited to 60 degrees, 90 degrees, 180 degrees, or another appropriate angle limit). The infrared data can include information related to blood flow, blood pressure, and other information that can be used to diagnose health of a patient.

Images of the foot or the leg of the person wearing the shoe are captured (604). In some implementations, the images are captured using a camera, such as a three dimensional camera. The camera can be configured to capture images of objects that are positioned between the particular toe wrap and a heel end of the shoe. For example, the camera can be embedded in one of the toe wraps of the shoe, and pointed toward a heel of the shoe.

The infrared data and the images are combined to create combined information about the leg or the foot (606). In some implementations, the infrared data are combined so that the infrared data is overlaid on the images collected by the camera. For example, the infrared data can be temporally and spatially synchronized with the images collected by the camera so as to show the infrared data that was captured at the time the images were collected, and to properly align the infrared data with the portion of the leg or foot from which the infrared data was collected. The temporal alignment can be achieved, for example, using timestamp information, watermarks, or other identifiers that can indicate when the infrared data and images were captured. The spatial alignment can be completed, for example, using reference markers or other indications as to how to visually align the infrared data and the images.

The combined information is output to present various physical changes to the foot or leg that were captured by the camera. For example, the combined information can be used to visually present blood flow through the foot or leg and/or other information that can be used to provide a person with a diagnosis or to aid a diagnosis. In some implementations, the combined information is output to a video display. In other implementations, the combined information can be output to a printer or another device that can provide a series of still images that include the combined information over a time period.

Figure 7:
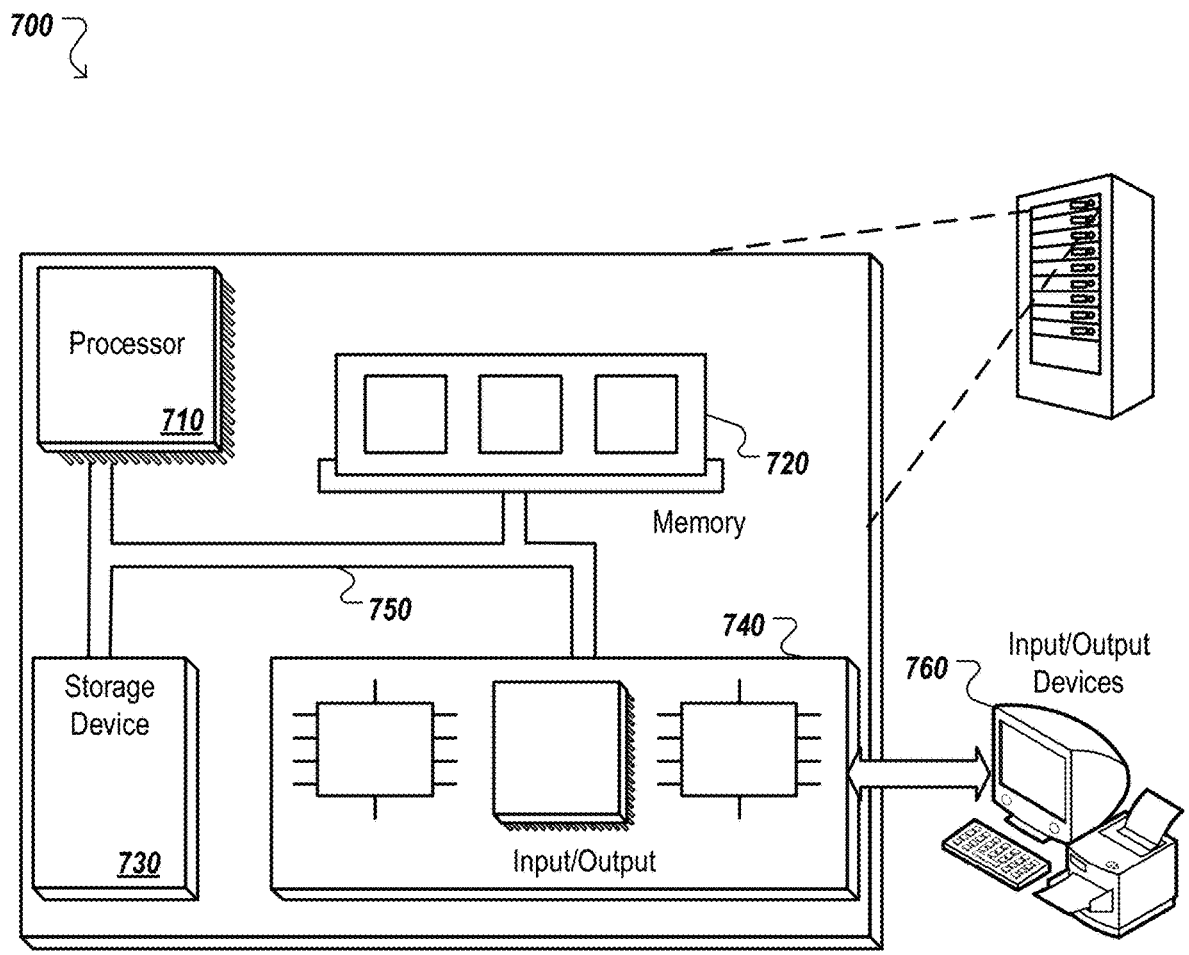
FIG. 7 is block diagram of an example computer system.

FIG. 7 is block diagram of an example computer system 700 that can be used to perform operations described above. The system 700 includes a processor 710, a memory 720, a storage device 730, and an input/output device 740. Each of the components 710, 720, 730, and 740 can be interconnected, for example, using a system bus 750. The processor 710 is capable of processing instructions for execution within the system 700. In one implementation, the processor 710 is a single-threaded processor. In another implementation, the processor 710 is a multi-threaded processor. The processor 710 is capable of processing instructions stored in the memory 720 or on the storage device 730.

The memory 720 stores information within the system 700. In one implementation, the memory 720 is a computer-readable medium. In one implementation, the memory 720 is a volatile memory unit. In another implementation, the memory 720 is a non-volatile memory unit.

The storage device 730 is capable of providing mass storage for the system 700. In one implementation, the storage device 730 is a computer-readable medium. In various different implementations, the storage device 730 can include, for example, a hard disk device, an optical disk device, a storage device that is shared over a network by multiple computing devices (e.g., a cloud storage device), or some other large capacity storage device.

The input/output device 740 provides input/output operations for the system 700. In one implementation, the input/ output device 740 can include one or more of a network interface device, e.g., an Ethernet card, a serial communication device, e.g., and RS-232 port, and/or a wireless interface device, e.g., and 802.11 card. In another implementation, the input/output device can include driver devices configured to receive input data and send output data to other input/output devices, e.g., keyboard, printer and display devices 760. Other implementations, however, can also be used, such as mobile computing devices, mobile communication devices, set-top box television client devices, etc.

Although an example processing system has been described in FIG. 7, implementations of the subject matter and the functional operations described in this specification can be implemented in other types of digital electronic circuitry, or in computer software, firmware, or hardware, including the structures disclosed in this specification and their structural equivalents, or in combinations of one or more of them.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A device comprising:
   a shoe sole; and
   a set of toe wraps engaged with the shoe sole; and
   at least one infrared device rotatably connected to a particular toe wrap among the set of toe wraps.

2. The device of claim 1, wherein the shoe sole comprises:
   a bottom layer;
   an intermediate layer; and
   a top layer.

3. The device of claim 2, wherein the intermediate layer includes one or more computing components that facilitate collection of information from sensors included in, or attached to, the device.

4. The device of claim 3, wherein the sensors include a three-dimensional camera and the infrared device.

5. The device of claim 2, wherein the top layer includes one or more pressure sensors.

6. The device of claim 1, wherein the infrared device is rotatable across at least one hundred eighty degrees.

7. The device of claim 1, wherein the set of toe wraps includes at least one toe wrap that comprises a camera that is arranged to capture images of objects that are positioned between the at least one toe wrap and a heel end of the shoe sole.

8. The device of claim 7, wherein the device includes one or more processors that combine information obtained from each of the infrared device and the camera.

9. The device of claim 8, wherein the one or more processors output the combined information from the infrared device and the camera to a display device, wherein the combined information visually presents various physical changes to a foot or leg that was captured by the camera.

10. The device of claim 9, wherein the physical changes include at least blood flow as detected using the infrared device.

11. A system comprising:
    one or more data processing apparatus; and
    a diagnostic device including:
      a shoe sole; and
      a set of toe wraps engaged with the shoe sole; and
      at least one infrared device rotatably connected to a particular toe wrap among the set.

12. The system of claim 11, wherein the shoe sole comprises:
    a bottom layer;
    an intermediate layer; and
    a top layer.

13. The system of claim 12, wherein the intermediate layer includes one or more computing components that facilitate collection of information from sensors included in, or attached to, the device.

14. The system of claim 13, wherein the sensors include a three-dimensional camera and the infrared device.

15. The system of claim 12, wherein the top layer includes one or more pressure sensors.

16. The system of claim 11, wherein the set of toe wraps includes at least one toe wrap that comprises a camera that is arranged to capture images of objects that are positioned between the at least one toe wrap and a heel end of the shoe sole.

17. The system of claim 16, wherein the one or more dat processing apparatus are configured to combine information obtained from each of the infrared device and the camera.

18. The system of claim 17, wherein the one or more data processing apparatus output the combined information from the infrared device and the camera to a display device, wherein the combined information visually presents various physical changes to a foot or leg that was captured by the camera.

19. A method, comprising:
    capturing, by an infrared device rotatably connected to a particular toe wrap among a set of toe wraps of a shoe, infrared data of a foot or leg of a person wearing the shoe;
    capturing, by a camera arranged to capture images of objects that are positioned between the particular toe wrap and a heel end of the shoe, images of the foot or the leg of the person wearing the shoe;
    combining the infrared data and the images to create combined information about the foot or the leg of the person wearing the shoe; and
    outputting the combined information to present various physical changes to the foot or the leg that were captured by the infrared device.

20. The method of claim 19, wherein the physical changes include at least blood flow as detected using the infrared device.

* * * * *